United States Patent
Tajbakhsh et al.

(10) Patent No.: US 11,725,250 B2
(45) Date of Patent: Aug. 15, 2023

(54) EARLY LUNG CANCER DETECTION BY DNA METHYLATION PHENOTYPING OF SPUTUM-DERIVED CELLS

(71) Applicants: Cedars-Sinai Medical Center, Los Angeles, CA (US); The Regents of the University of California, Oakland, CA (US); UNITED STATES GOVERNMENT REPRESENTED BY THE DEPARTMENT OF VETERANS AFFAIRS, Washington, DC (US)

(72) Inventors: Jian Tajbakhsh, Encino, CA (US); Fariborz Mortazavi, Porter Ranch, CA (US)

(73) Assignees: Cedars-Sinai Medical Center, Los Angeles, CA (US); the Regents of the University of California, Oakland, CA (US); U.S. Govt Department of Veterans Affairs, Washington, DC (US)

( * ) Notice: Subject to any disclaimer, the term of this patent is extended or adjusted under 35 U.S.C. 154(b) by 246 days.

(21) Appl. No.: 17/180,433

(22) Filed: Feb. 19, 2021

(65) Prior Publication Data
US 2021/0172028 A1 Jun. 10, 2021

Related U.S. Application Data

(62) Division of application No. 15/507,668, filed as application No. PCT/US2015/047567 on Aug. 28, 2015, now Pat. No. 10,961,587.

(60) Provisional application No. 62/043,346, filed on Aug. 28, 2014.

(51) Int. Cl.
| | | |
|---|---|---|
| G01N 33/48 | (2006.01) | |
| C12Q 1/6886 | (2018.01) | |
| G01N 33/574 | (2006.01) | |
| G01N 1/30 | (2006.01) | |

(52) U.S. Cl.
CPC ..... C12Q 1/6886 (2013.01); G01N 33/57423 (2013.01); *C12Q 2600/154* (2013.01); *G01N 1/30* (2013.01); *G01N 2440/12* (2013.01); *G01N 2800/50* (2013.01)

(58) Field of Classification Search
None
See application file for complete search history.

(56) References Cited

U.S. PATENT DOCUMENTS

| | | |
|---|---|---|
| 5,037,207 A | 8/1991 | Tomei |
| 6,007,996 A | 12/1999 | McNamara |
| 10,961,587 B2 | 3/2021 | Center et al. |
| 2008/0247628 A1 | 10/2008 | Ramsing |
| 2009/0280485 A1 | 11/2009 | Flores |
| 2010/0111396 A1 | 5/2010 | Boucheron |
| 2010/0151468 A1* | 6/2010 | Esteller ............ G01N 33/57496 435/6.12 |
| 2010/0304380 A1* | 12/2010 | Tajbakhsh .......... G01N 33/5308 435/6.14 |
| 2013/0315946 A1 | 11/2013 | Kuo |
| 2014/0038183 A1 | 2/2014 | Yegnasubramanian |
| 2014/0213475 A1 | 7/2014 | Lawrence |
| 2017/0283881 A1 | 10/2017 | Center et al. |

FOREIGN PATENT DOCUMENTS

| | | |
|---|---|---|
| AU | 2015308620 A1 | 3/2017 |
| AU | 2015308620 A1 | 10/2021 |
| BR | 11-2017004098-0 A2 | 12/2017 |
| CA | 2959507 A1 | 3/2016 |
| CN | 107002125 A1 | 8/2017 |
| EP | 3186396 A1 | 7/2017 |
| IL | 250830 B | 8/2020 |
| JP | 2017-526921 A | 9/2017 |
| JP | 6696974 | 4/2020 |
| KR | 2017-0065027 A | 6/2017 |
| KR | 102412396 B1 | 6/2022 |
| MX | 201702654 A | 8/2017 |
| UA | 40065 * | 3/2009 |
| WO | WO 2004/104582 A1 | 12/2004 |
| WO | WO 2007/087653 A1 | 8/2007 |

(Continued)

OTHER PUBLICATIONS

Ho et al., Nuclear DNA methylation and chromatin condensation phenotypes are distinct between normally proliferating/aging, rapidly growing/immortal, and senescent cells, Oncotarget, 2013, vol. 4(3), pp. 474-493.

De Capoa et al., DNA demathylation is directly related to tumor progression: Evidence in normal, pre-malignant and malignant cells from uterine cervix samples, Oncology Reports, 2003, vol. 10(3), pp. 545-549.

De Capoa et al., Methylation levels of normal and chronic lymphocytic leukemia B lympocytes: computer-assisted quantitative analysis of anti-5-methylcytosine antibody binding to individual nuclei, Cytometry, vol. 36(2), 1999, pp. 157-159.

(Continued)

*Primary Examiner* — Anna Skibinsky
(74) *Attorney, Agent, or Firm* — Nixon Peabody LLP

(57) ABSTRACT

In certain embodiments, this application discloses methods for detecting lung cancer. The method includes characterization of cells extracted from human sputum, which is a valuable tissue surrogate and source of upper respiratory cells that become cancerous early in the process of lung cancer development. The method includes the staining of extracted cells with fluorescent reporters that produce a specific pattern in the nuclei of labeled cells, which can be made visible by light microscopy. The pattern is relevant to a type of epigenetic coding of DNA known as DNA methylation, which changes in specific cells of the lung during cancer development, in comparison to normal respiratory cells.

18 Claims, 8 Drawing Sheets

(56) References Cited

FOREIGN PATENT DOCUMENTS

| WO | WO 2013/090588 A1 | 6/2013 |
|---|---|---|
| WO | WO 2016/033542 A | 3/2016 |

OTHER PUBLICATIONS

Exam Report for EP 15835681.6 dated Mar. 1, 2022, 3 pages.
JP 2017-511687 Reasons for Rejection dated Jun. 5, 2019.
Exam Report for MX/a/2017/002654 dated Apr. 23, 2021.
Exam Report for CN 201580056975.9 dated Jun. 2, 2020.
Exam Report for CN 201580056975.9 dated Mar. 25, 2021.
Isreal Office Action dated Jan. 21, 2020, 6 pages.
Isreal Office Action dated Dec. 25, 2018, 7 pages.
Gertych et al., Measuring Topology of Low-Intensity DNA Methylation Sites for High Throughput Assessment of Epigenetic Drug-Induced Effects in Cancer Cells, Exp Cell Res., 2010, vol. 316(19), pp. 3150-3160.
Gertych et al., Homogeneity Assessment of Cell Populations for High Content Screening Platforms, Information Technologies in Biomedicine, 2010, vol. 69, Abstract only.
Tajbakhsh et al., Three-dimensional quantitative DNA methylation imaging for chromatin texture analysis in pharmapigenomics and toxioepigenomics, pigenomics: From Chromatin Biology to Therapeutics, 2012.
Tajbakhsh et al., Early In Vitro Differentiation of Mouse Definitive Endoderm Is Not Correlated with Progressive Maturation of Nuclear DNA Methylation Patterns, Plos One, 2011, vol. 6(7), pp. 1-13.
Tajbakhsh et al., Dynamic Heterogeneity of DNA Methylation and Hydroxymethylation in Embryonic Stem Cell Populations Captured by Single-Cell 3D High-Content Analysis, Exp Cell Res., 2015, vol. 332(2), pp. 190-201.
Exam Report for CA 2,959,507 dated Jun. 3, 2022, 4 pages.
OH, J. H. et al., "Nuclear DNA Methylation and Chromatin Condensation Phenotypes Are Distinct Between Normally Proliferating/Aging, Rapidly Growing/Immortal, and Senescent Cells," Oncotarget, 4(3): 474-493, Mar. 26, 2013.
Australian Examination Report in Australian Patent Application No. AU 2015308620, dated Mar. 31, 2021 (9 pages).
Mexican Office Action in Mexican Patent Application No. MX/a/2017/002654, dated Apr. 23, 2021 (6 pages w/English translation).
Extended European Search Report in European Patent Application No. EP 15835681.6, dated Dec. 6, 2018 (7 pages).
International Search Report and Written Opinion in International Application No. PCT/U82015/047567, dated Dec. 7, 2015 (11 pages).
International Preliminary Report on Patentability in International Application No. PCT/U82015/047567, dated Feb. 28, 2017 (10 pages).
Ansiowicz et al., "A High-Throughput and Sensitive Method to Measure Global DNA Methylation: Application in Lung Cancer," BMC Cancer 8(222): 1-12 (2008).
Arens et al., "Nuclear Localization of Heterochromatic Regions Varies in Hyperplastic and Preneoplastic Lesions of the Breast,"Verh. Dtsch. Ges. Path 89: 191-194 (2005).
Belinsky et al., "Aberrant promoter methylation in bronchial epithelium and sputum from current and former smokers,"Cancer Res. 62: 2370-2377 (2002).
Belinsky et al., "Gene promoter hypermethylation as a biomarker in lung cancer," Nat. Rev. Cancer, pp. 707-717 (2004).
Belinsky et al., "Gene promoter methylation in plasma and sputum increases with lung cancer risk,"Clin. Cancer Res. 11, pp. 6505-6511 (2005).
Belinsky et al., "Predicting gene promoter methylation in non-small-cell lung cancer by evaluating sputum and serum,"Br. J. Cancer 96, pp. 1278-1283 (2007).
Chan et al., "Noninvasive Detection of Cancer-Associated Genome-Wide Hypomethylation and Copy Number Aberrations by Plasma DNA Bisulfite Sequencing," PNAS 110(47): 18761-18768 (2013).
Donninger et al., "The rassf1a tumor suppressor,"J. Cell. Sci. 120, pp. 3163-3172 (2007).
Foster et al., "Inactivation of p16 in human mammary epithelial cells by cpg island methylation,"Mol. Cell Biol. 18, pp. 1793-1801 (1998).
Gertych et al., "Automated Quantification of DNA Demethylation Effects in Cells via 3D Mapping of Nuclear Signatures and Population Homogeneity," Assessment Cytometry Part A, 75(7): 569-583 (2009).
Gertych et al., "3-D DNA Methylation Phenotypes Correlate with Cytotoxicity Levels in Prostate and Liver Cancer Cell Models,"BMC Pharmacology and Toxicoloy 14(11): 1-21 (2013).
Jones et al., "The fundamental roles of epigenetic events in cancer,"Nat. Rev. Genet. 3, pp. 415-428 (2002).
Kim et al., "Sputum-Based Molecular Biomarkers for the Early Detection of Lung Cancer, Limitations and Promise,"Cancer 3, pp. 2975-2989 (2011).
Liu et al., "Hypermethylation of p16ink4a in Chinese lung cancer patients: Biological and clinical implications," Carcinogenesis 24, pp. 1897-1901 (2003).
Patra et al., "DNA methylation-mediated nucleosome dynamics and oncogenic ras signaling: Insights from fas, fas igand and rassf1a,"FEBS J. 275, pp. 5217-5235 (2008).
Pegg, A. E., "Repair of o(6)-alkylguanine by alkyltransferases,"Mutat. Res. 462, pp. 83-100 (2000).
Scheicher et al., "Sputum Induction: Review of Literature and Proposal for a Protocol,"Sao Paulo Med. J., 121(5): 213-219 (2003).
Schmiemann et al., "In situ Detection of Global DNA Hypomethylation in Exfoliative Cytology of Patients with Suspected Bladder and Lung Cancer,"Pathology—Research and Practice 200(4): 356-359 (2004).
Tajbakhsh et al., "Covisualization of Methylcytosine, Global DNA, and Protein Biomarkers for In Situ 3D DNA Methylation Phenotyping of Stem Cells Imaging and Tracking Stem Cells,"Methods in Molecular Biology 1052, pp. 77-88 (2013).
Tsou et al., "DNA methylation analysis: a powerful new tool for lung cancer diagnosis,"Oncoene 21, pp. 5450-5461 (2002).
Centers for Disease Control National Health Interview Survey Glossary, https://www.cdc.gov/nchs/nhis/tobacco/tobacco_glossary.htm, accessed May 11, 2018.
Kin et al., "Sputum-Based Molecular Biomarkers for the Early Detection of Lung Cancer: Limitations and Promise,"Cancers 3: 2975-2989 (2011).

* cited by examiner

EARLY LUNG CANCER DETECTION BY DNA METHYLATION PHENOTYPING OF SPUTUM-DERIVED CELLS

CROSS-REFERENCE TO RELATED APPLICATIONS

This application is a divisional application of U.S. application Ser. No. 15/507,668, filed Feb. 28, 2017, which is a National Phase of International Application No. PCT/US2015/047567, filed Aug. 28, 2015, which designated the U.S. and that International Application was published under PCT Article 21(2) in English, which claims priority under 35 U.S.C. § 119(e) to U.S. Provisional Application No. 62/043,346, filed Aug. 28, 2014, each of which is hereby incorporated by reference herein in its entirety.

FIELD OF THE INVENTION

The present invention generally relates to the diagnosis, prognosis, and treatment of cancer, and especially lung cancer.

BACKGROUND

The following description includes information that may be useful in understanding the present invention. It is not an admission that any of the information provided herein is prior art, or relevant to the presently claimed invention.

Traditional methods of screening for lung cancer include mediastinoscopy, and radiographic methods, such as computed tomography (CT) and positron emission tomography (PET). Unfortunately, these methods are expensive and/or require exposing patients to potentially harmful ionizing radiation. In addition, scans are not reliable for detecting early-stage lung cancer that may be too small to detect by radiographic methods, but nonetheless pose significant danger to a patient. This is especially relevant, because early-stage lung cancer detection is associated with a much more favourable prognosis than late-stage detection.

There is clearly a need in the art for a safe, relatively inexpensive, and sensitive method for detecting lung-cancer, especially at an early stage.

SUMMARY OF THE INVENTION

In various embodiments, the invention teaches a method for determining if a cell is cancerous or precancerous, including: determining a global 5-methylcytosine (5mC) content and/or spatial nuclear co-distribution of 5mC and global DNA (gDNA) in a nucleus of the cell; and determining that the cell is cancerous or precancerous if the global 5mC content and/or spatial nuclear co-distribution of 5mC and gDNA in the nucleus of the cell is significantly different from a non-cancerous or non-precancerous reference cell and/or a non-cancerous or non-precancerous reference cell population, or determining that the cell is not cancerous or not precancerous if the global nuclear 5mC content and/or spatial nuclear co-distribution of 5mC and gDNA are not significantly different from those of a non-cancerous or non-precancerous reference cell and/or a non-cancerous or non-precancerous reference cell population. In some embodiments, the cell is determined to be cancerous or precancerous if the global 5mC content is significantly lower than the non-cancerous or non-precancerous reference cell and/or non-cancerous or non-precancerous reference cell population. In certain embodiments, the cell is obtained from a biological sample. In some embodiments, the biological sample includes sputum. In certain embodiments, the sputum includes respiratory cells. In certain embodiments, the cancerous cell or precancerous cell is of lung cancer origin. In some embodiments, the biological sample is obtained from a subject who has a history of smoking cigarettes. In some embodiments, the biological sample is obtained from a subject who does not have a history of smoking cigarettes. In some embodiments, the biological sample is obtained from a subject who has lung cancer and has not been treated for lung cancer. In certain embodiments, the biological sample is obtained from a subject who has received a lung cancer treatment selected from the group consisting of: radiation therapy, chemotherapy, surgery, and combinations thereof. In some embodiments, global 5mC and gDNA contents are determined with a microscope after the cell has been subjected to (a) immunofluorescence staining with an antibody specific for 5mC, and (b) counterstaining with 4',6-diamidino-2-phenylindole (DAPI). In certain embodiments, spatial nuclear co-distribution of 5mC and gDNA is determined with a microscope after the cell has been subjected to (a) immunofluorescence staining with an antibody specific for 5mC, and (b) counterstaining with 4',6-diamidino-2-phenylindole (DAPI). In some embodiments, the sputum sample was obtained from a subject by a method that includes administering hypertonic saline into the subject's respiratory tract; and collecting a quantity of sputum that is expelled from the subject as the result of inhaling said hypertonic saline. In some embodiments, the hypertonic saline is administered via a nebulizer. In certain embodiments the hypertonic saline is 3-5% NaCl. In certain embodiments, the microscope is a confocal scanning microscope with a resolution equal to or less than 500 nanometers.

In various embodiments, the invention teaches a method that includes obtaining a biological sample from a subject, wherein the biological sample includes a cell; determining a global 5-methylcytosine (5mC) content and/or spatial nuclear codistribution of 5mC and global DNA (gDNA) in a nucleus of the cell; determining that the cell is cancerous or precancerous if the global 5mC content and/or spatial nuclear codistribution of 5mC and gDNA in the nucleus of the cell is significantly different from a non-cancerous or non-precancerous reference cell and/or non-cancerous or non-precancerous cell population; and determining that the subject has a high risk of developing clinically verifiable cancer, if it is determined that the cell is cancerous or precancerous. In some embodiments, the method also includes treating the subject for cancer, if it is determined that the subject has a high risk for developing clinically verifiable cancer, or if it is determined that the subject has developed clinically verifiable cancer. In some embodiments, the biological sample includes sputum. In some embodiments, the sputum includes respiratory cells. In some embodiments, the cancerous cell or precancerous cell is of lung cancer origin. In certain embodiments, the subject has a history of smoking cigarettes. In some embodiments, the subject does not have a history of smoking cigarettes.

BRIEF DESCRIPTION OF THE DRAWINGS

Exemplary embodiments are illustrated in the referenced figures. It is intended that the embodiments and figures disclosed herein are to be considered illustrative rather than restrictive.

cytological specimen preparation/staining, (2) 3D-imaging of specimens, and (3) computational image/data analysis for specimen characterization.

Figure 2:
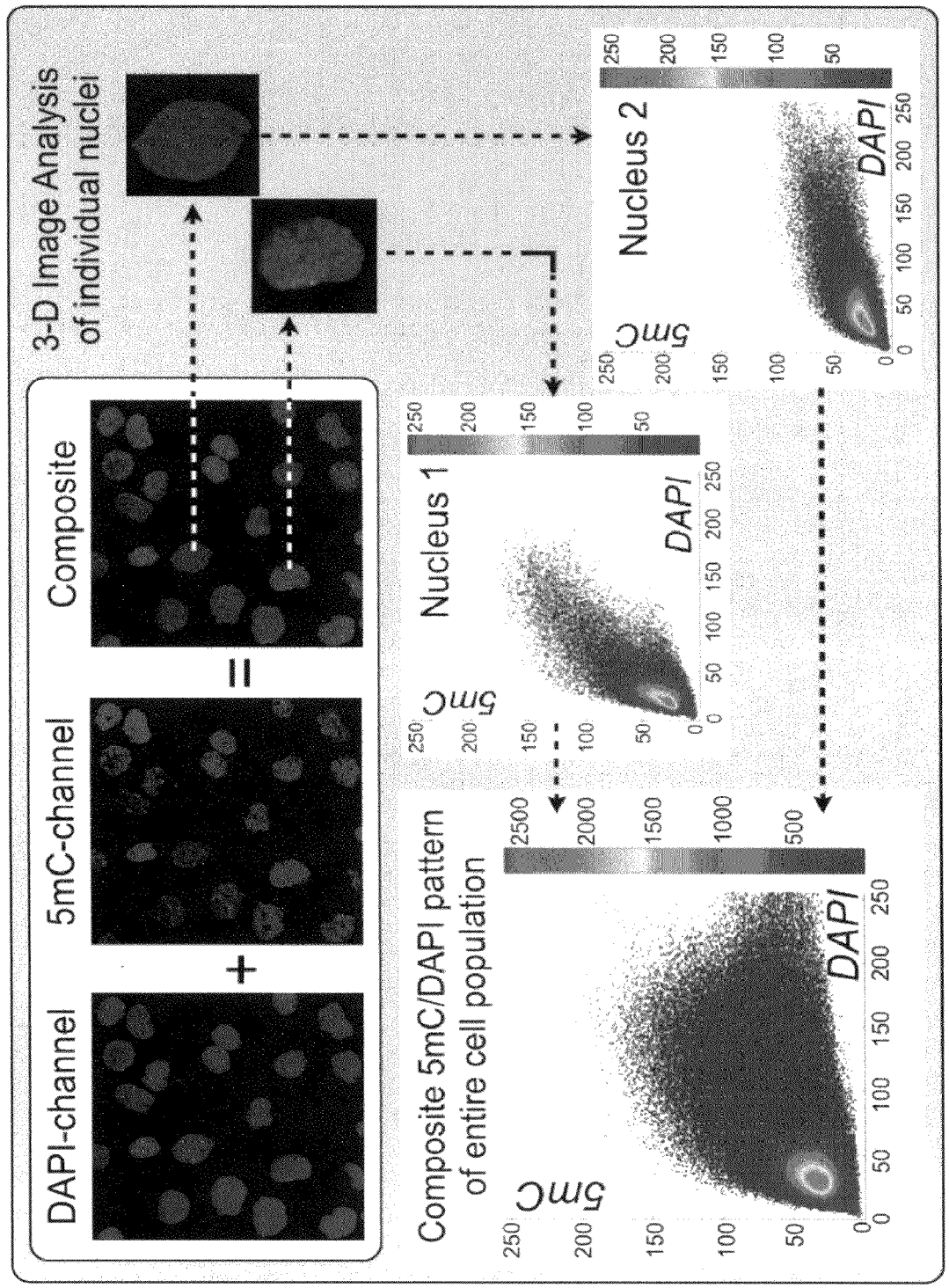

FIG. 2 demonstrates, in accordance with an embodiment of the invention, workflow of 3-D image analysis (example shown with DU145 human prostate cancer cells). Confocal 2D image stacks from the two channels of 5-methylcytosine (5mC) and 4',6-diamidino-2-phenylindole (DAPI) are loaded. DAPI represents global nuclear DNA (gDNA). Extracted nuclear 5mC/DAPI patterns are displayed as 2D density scatter plots of voxel-intensities of the two channels. Example patterns are shown for two selected nuclei. The 5mC/DAPI codistribution pattern of the entire population is created through superposition of patterns from all individual nuclei that could be distinct in appearance/statistics representing highly differential codistribution of nuclear 5mC and DAPI signals. Units indicated on the axes of the scatter plots are Arbitrary Intensity Units.

Figure 3:
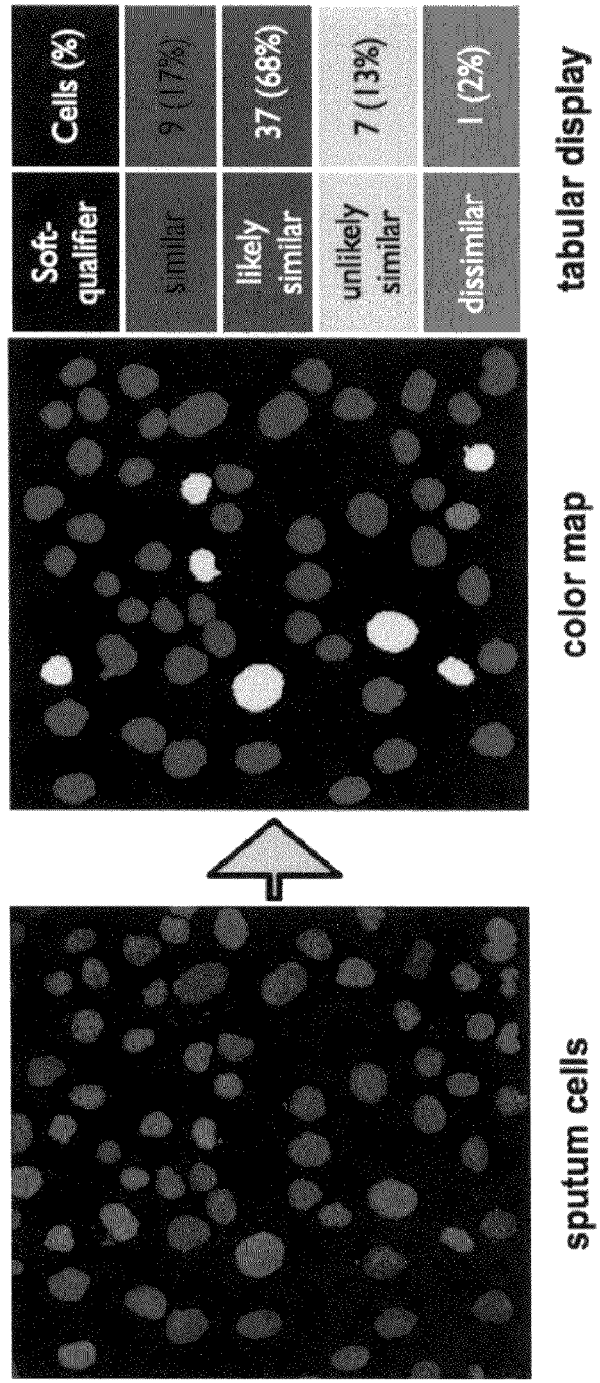

FIG. 3 demonstrates, in accordance with an embodiment of the invention, diagnostic output of 3D-qDMI (Left): characterization of the sputum cell population based on 5mC (green) and gDNA/DAPI (blue) texture features (DNA methylation phenotypes) in the fluorescence image. Cells can be categorized into different similarity degrees by "soft-qualifiers" that span increasing value ranges associated with color codes (Right). The 3D-qDMI software uses this coding to convert the original fluorescence image (across all confocal image layers) into a color map and a corresponding tabular display for better visualization and interpretation of the resulting data. The data leads to identification and enumeration of the different types of cells for determining the heterogeneity of DNA methylation phenotypes in cell populations.

Figure 4:
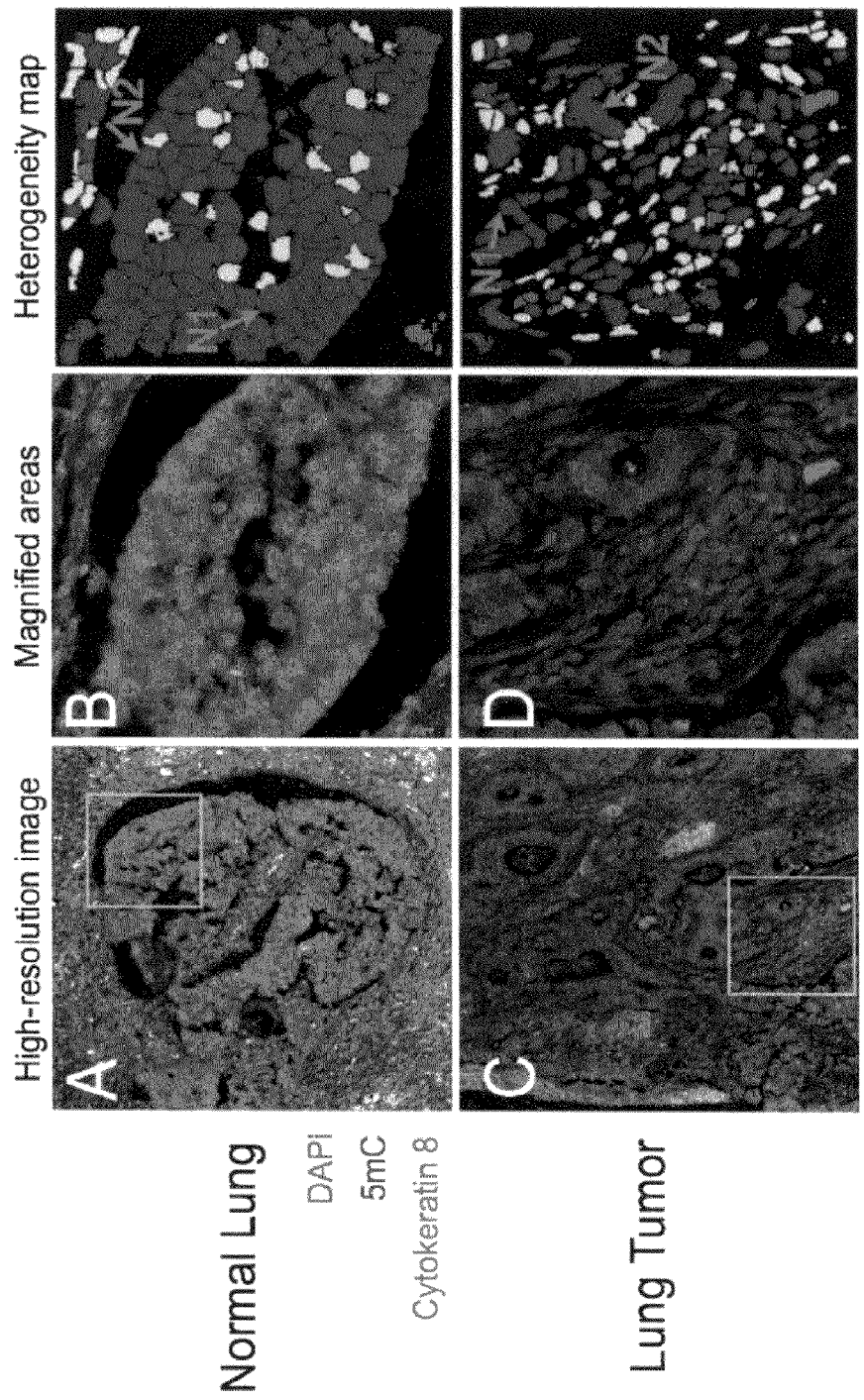

FIG. 4 demonstrates, in accordance with an embodiment of the invention, normal parenchyma and the humoral region of a fluorescently labeled section from a newly diagnosed, surgically resected lung cancer. Cell nuclei (blue) in normal lobules (A) and magnified boxed subarea (B) show higher degree of DNA methylation (5mC, green) compared with severely hypomethylated nuclei in ductal regions of the tumor (C) and magnified boxed subarea (D) on the same section; cytokeratin 8 (red) was used as a marker to delineate the epithelial compartments.

Figure 5A:
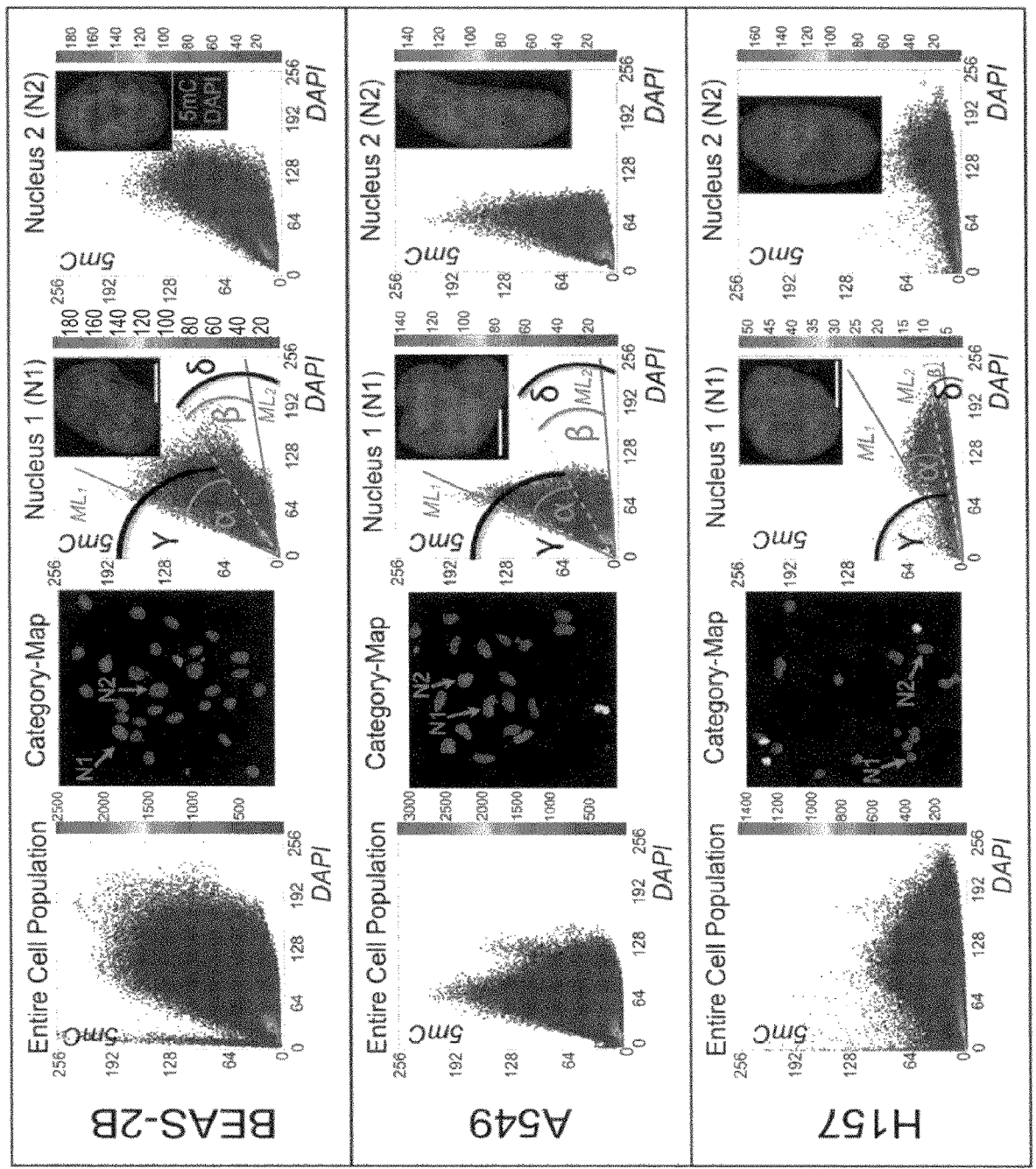
Figure 5B:
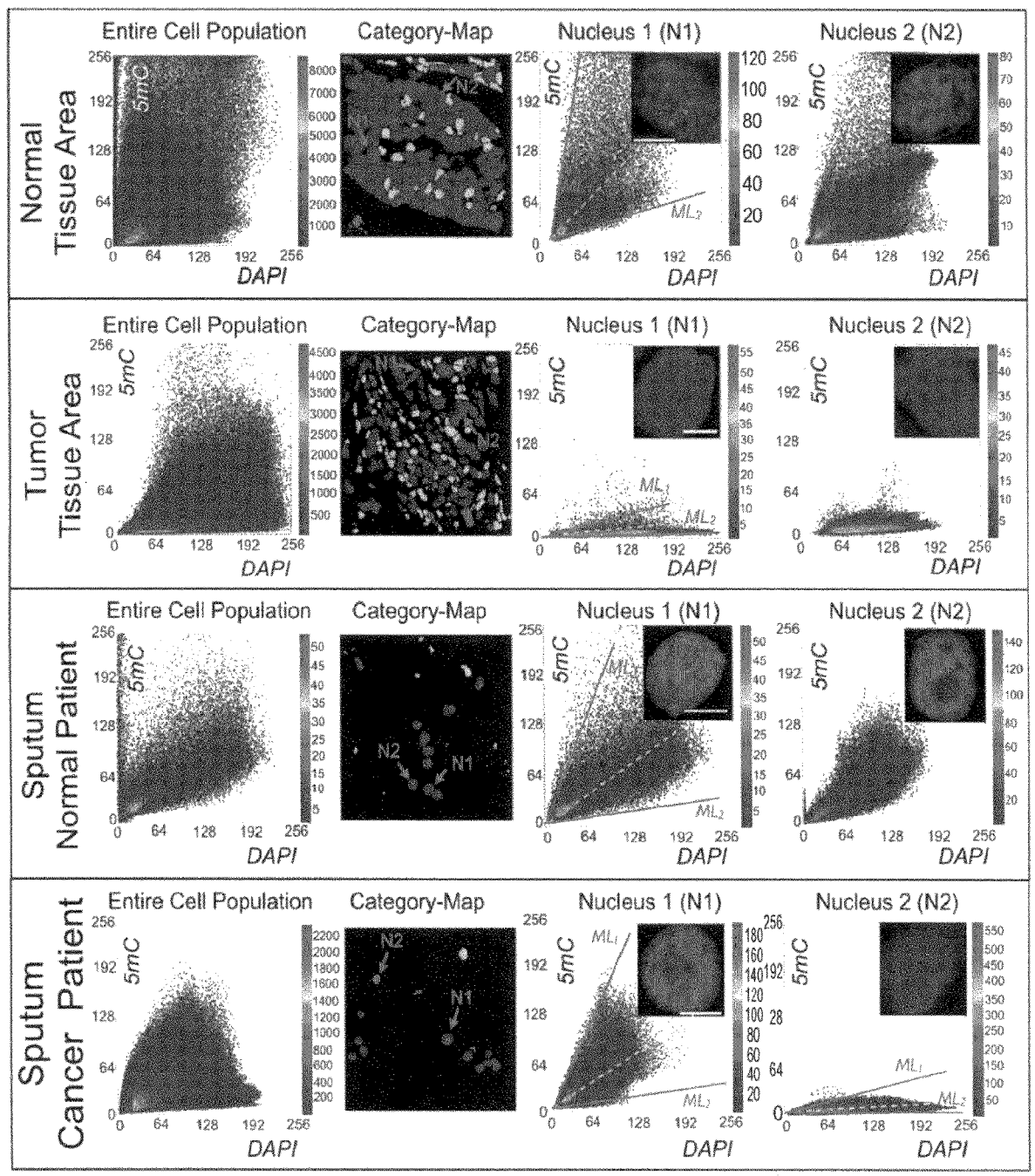

FIGS. 5A & 5B demonstrate, in accordance with an embodiment of the invention, global DNA methylation phenotyping of cells and tissues with 3D-qDMI. The method was able to successfully distinguish between the different cell types based on differential 5mC/DAPI distribution patterns (scatter plots): calculated and displayed as individual heat map scatter plots (DAPI=x-axis, 5mC=y-axis) for the entire cell population as the reference plot, as well as for each nucleus as shown for the selected nuclei N1 and N2 for each cell category. Non-small cell lung cancer (NSCLC) cell lines A549 and H157 display a reduction in global 5mC compared to immortalized epithelial respiratory cells (BEAS-2B). H157 cells, which are reported to have more metastatic potential than A549 cells, are even more hypomethylated (flatter curve). The same comparative relation can be found in surgically removed tissue from a lung cancer patient and adjacent normal lung tissue and also from matching sputum samples of the lung cancer patient versus the healthy person (with no cancer): The cytometric 5mC/DAPI signatures found in healthy sputum cells are very similar to the patterns seen in cells in the phenotypically normal area (see FIG. 3 for a real image) and BEAS-2B cells. In contrast, severe hypomethylation can be observed in a small number of sputum cells (N2-type)—in the background of a larger number of cells with normal 5mC-phenotype (N1-type)—of the cancer patient that matches signatures of cells from the tumoral region and the more aggressive H157 cell line (higher metastatic potential). In other words, the rare sputum cells with aberrant 5mC-phenotype have a strong resemblance with well-characterized aggressive cancer cells (in tumors and tumor-derived cell lines). The regression line (yellow-dashed) and the upper and lower signal borderlines ML1 and ML2 are characteristic and determine the four angles α, β, γ, and δ for each prototypic cell type. The resulting factor F=[(α/γ)×(β/δ)] is specific to each cell type. All cell populations show high homogeneity: i.e. high degree of 5mC-phenotype similarity between cells, as judged by the respective category-maps, and the similarity between the scatter plots of individual nuclei (N1 and N2) compared to the plot of the respective entire population. Units indicated on the axes of the scatter plots in FIGS. 5A and 5B are Arbitrary Intensity Units.

Figure 6:
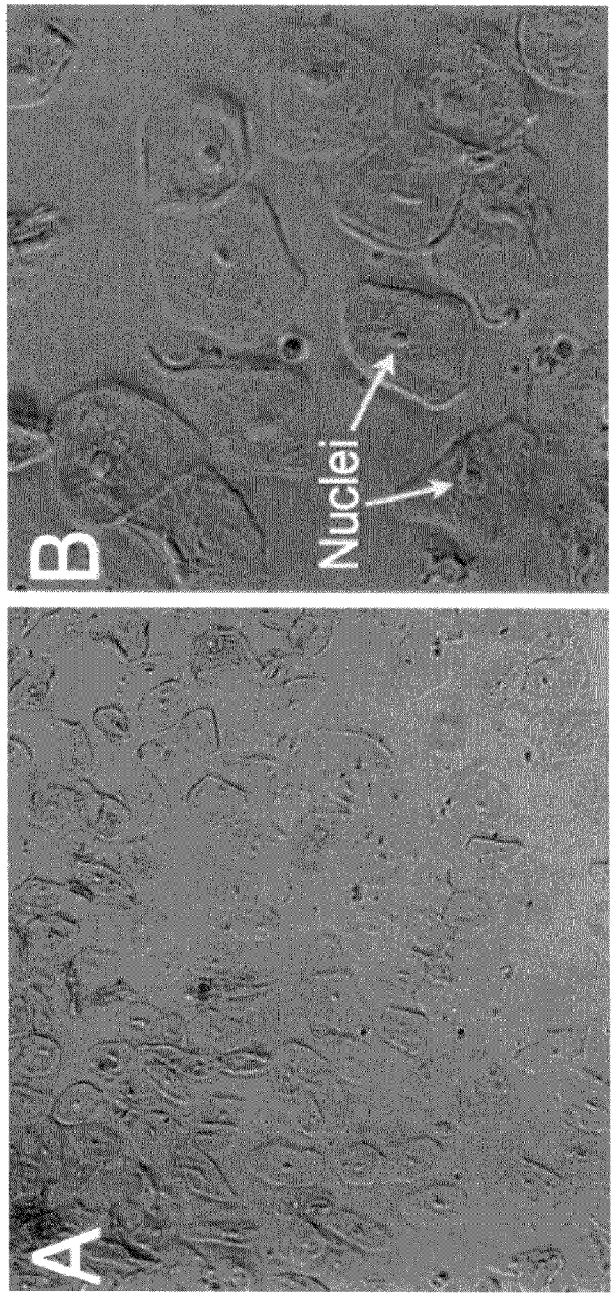

FIG. 6 demonstrates, in accordance with an embodiment of the invention, a bright field microscopic image of relatively flat human epithelial cells, derived from induced sputum. (A) Cells were isolated from mucus-liquid fraction of sputum and captured on a glass slide using culturing techniques. A few milliliters of sputum can contain hundreds to thousands of cells. (B) Magnification of an area reveals the relative substructure of layered cells that are mononuclear.

Figure 7:
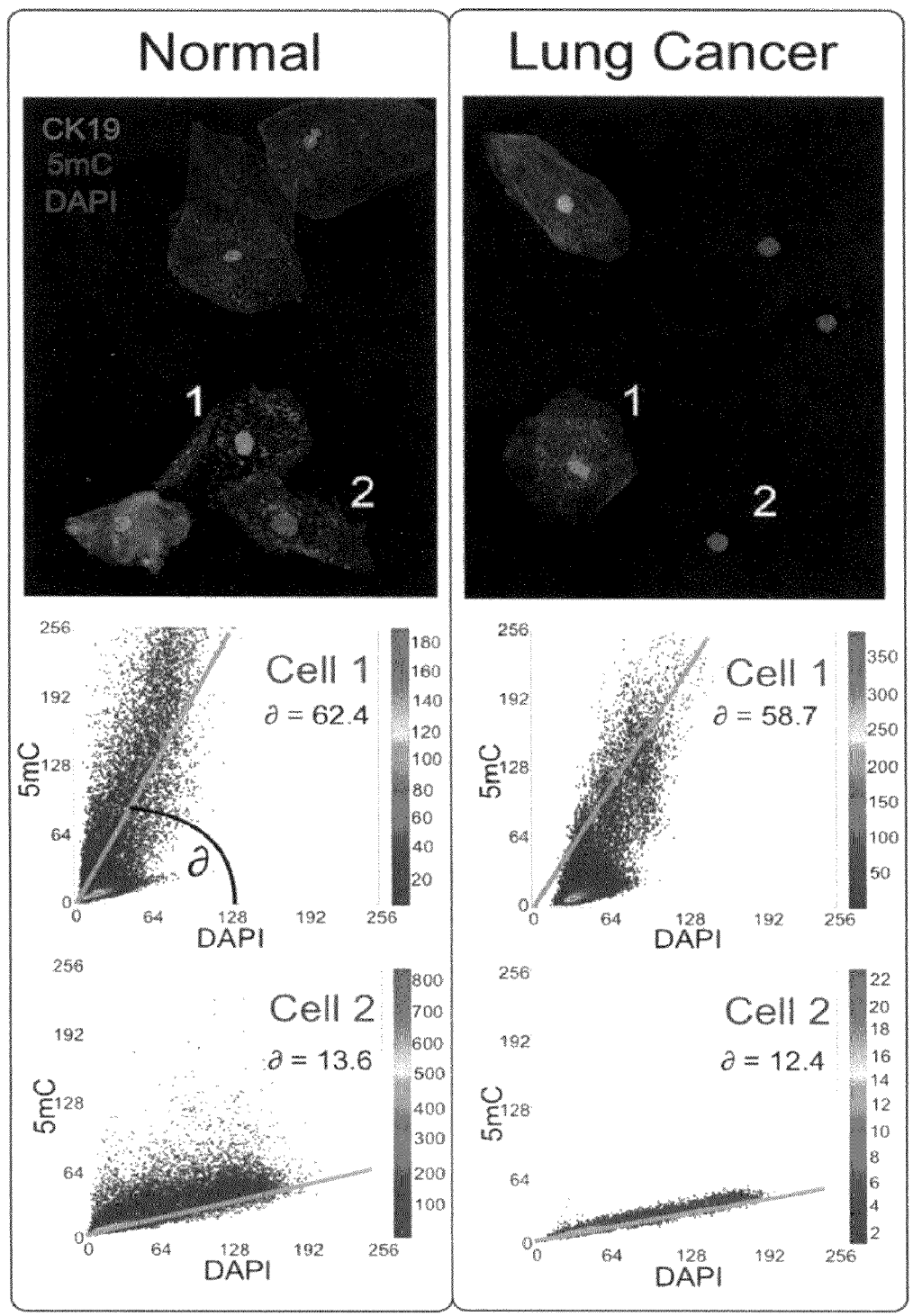

FIG. 7 demonstrates, in accordance with an embodiment of the invention, confocal images of fluorescently labeled sputum-derived human cells. The cytoplasm is delineated by the epithelial-cell marker cytokeratin 19 (CK19, in red), cell nuclei are delineated by DAPI (in blue), and global nuclear DNA methylation is visualized by an antibody specific to 5mC (in green). The sputum of healthy individuals (control) contains an overwhelming majority of highly methylated cells (type 1, left column) and sporadically a few CK19-positive hypomethylated cells (type 2, left column). It is assumed that the hypomethylation is facultative to the early stage after cell division. In contrast, the sputum of a lung cancer patient additionally contains a significant number of round cells with almost no cytoplasm (type 2, right column). These cells are CD34/CD45-negative, indicating that they are not of hematopoietic and/or leukocytic nature. The respective nuclear 5mC/DAPI codistribution patterns, presented as scatter plots, show that normally methylated (type 1) cells in both sputum-donor groups display a steep regression line ($\partial > 45°$), whereas hypomethylated cells (type 2) produce a much flatter regression line ($\partial \ll 45°$). Moreover, a typical signature of the lung cancer-specific rounded cells is the much less dispersed and narrow co-distribution of 5mC and DAPI. Units indicated on the axes of the scatter plots are Arbitrary Intensity Units.

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22$^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3rd ed., revised ed., J. Wiley & Sons (New York, N.Y. 2006); Smith,

*March's Advanced Organic Chemistry Reactions, Mechanisms and Structure* 7th ed., J. Wiley & Sons (New York, N.Y. 2013); Singleton, *Dictionary of DNA and Genome Technology* 3rd ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* 2nd ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 July, 6(7):511-9; Queen and Selick, *Humanized immunoglobulins*, U.S. Pat. No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Indeed, the present invention is in no way limited to the methods and materials described. For purposes of the present invention, certain terms are defined below.

"Conditions" and "disease conditions," as used herein, may include but are in no way limited to those conditions that are associated with cancer or pre-cancer, including, but in no way limited to lung cancer, cancer of the head or neck, cancer of the upper aerodigestive tract, cervical cancer, ovarian cancer, urethral cancer, bladder cancer, and colorectal cancer.

"Mammal," as used herein, refers to any member of the class Mammalia, including, without limitation, humans and nonhuman primates such as chimpanzees and other apes and monkey species; farm animals such as cattle, sheep, pigs, goats and horses; domesticated mammals, such as dogs and cats; laboratory animals including rodents such as mice, rats and guinea pigs, and the like. The term does not denote a particular age or sex. Thus, adult and newborn subjects, whether male or female, are intended to be included within the scope of this term. While cancer or precancer can be detected in humans according to the inventive methods described herein, detecting cancer in any mammal according to the inventive methods is within the scope of the invention.

The terms "global 5mC" and "5mC content" are used herein interchangeably, and in each case can be defined as the total amount of 5-methylcytosine molecules present in a cell nucleus.

The term "global DNA (gDNA)" as used herein means the total amount of DNA present in a cell nucleus.

The term "clinically verifiable cancer" as used herein means cancer that is verifiable by traditional means of cancer detection, including but not limited to minimally-invasive mediastinoscopy, noninvasive radiographic methods, such as computed tomography (CT), positron emission tomography (PET), magnetic resonance imaging (MM), and the like.

By way of additional background, it is becoming more and more evident that epigenetic mechanisms such as DNA methylation have a strong influence in the development of multi-cellular systems, in their healthy maintenance and in their structural and functional decline during aging and at an accelerated rate by diseases such as cancer, alongside with and even without the coexistence of genetic mutations. Therefore, methods for measuring DNA methylation are vital in understanding these mechanisms in efforts for combating cancers and securing healthy aging. There is no doubt that imaging, alongside with molecular techniques, is playing an indispensable role in the differential quantification of DNA methylation in cells and tissues.

Measuring changes in DNA methylation is valuable, since it correlates with early events in carcinogenesis and tumor progression, and can serve as a signature in early diagnostics and therapeutic monitoring. In this sense, the inventors' approach, as described in certain embodiments herein, to apply quantitative DNA methylation imaging for early detection of lung cancer revives the idea of in situ measuring epigenetic features such as DNA methylation in exfoliated respiratory cells for their characterization, for a cell-by-cell based pathological diagnosis.

DNA methylation imaging, which was introduced for tissue characterization towards the end of the 1990s did not gain much popularity in comparison to contemporaneously developed molecular methods, including PCR-based, array-based, sequencing, high-pressure liquid chromatography (HPLC), and mass spectrometry, for two reasons: (i) it was applied in combination with radio-labeled or enzymatic reporters for detection, which either lack sensitivity, multiplexing capability or affect repeatability/consistency of the assay, and (ii) did not provide enough significance in differential results due to low image resolution. Enormous improvements in high-resolution imaging and computational capacity within recent years have been supportive to the development of more sophisticated tools in cell-based assays that can be applied to biomedical research and clinical diagnosis. This was also a pre-requisite for the development of 3D-qDMI to revisit the concept of nondestructive imaging of large-scale changes on the higher-order chromatin structure by epigenetic reporters such global DNA methylation.

In short, the 3D-qDMI approach described herein is especially advantageous because it allows for (1) high-resolution imaging of 5-methylcytosine (5mC) and global DNA (gDNA), and (2) digital extraction of three 5mC-relevant features as diagnostic signatures for early lung cancer detection: (i) the 5mC load (content), (ii) the spatial nuclear codistribution of 5mC and gDNA, and (iii) measurement of cell-population heterogeneity based on the first two 5mC features, in order to characterize respiratory epithelial cells in sputum samples (FIG. 2).

Compared to current molecular approaches and a few previous low-resolution imaging-based attempts that either average 5mC measurements across a large population of cells or only measure mean 5mC intensity values in cell nuclei, 3D-qDMI leverages the extraction of differential 5mC-relevant information by considering secondary effects of DNA methylation imbalances that occur throughout cellular transformation, especially hypomethylation of gDNA. In particular the latter mechanism elicits reorganization of the genome within cell nuclei, affecting nuclear architecture. This phenomenon is well described in basic cell biological research, but has not yet been exploited well in cancer pathology. The image analysis applied in some embodiments of the inventive method covers this gap and displays the relevant changes as intensity distribution of the two types of signals that reflect said phenomena: (a) 5mC-signals created through immunofluorescence targeting and (b) gDNA represented by DAPI-signals that are generated by subsequent counter-staining of the same cells, as DAPI intercalates into AT-rich DNA the main component of highly repetitive and compact heterochromatic sequences. Overall, the method results in images that represent maps of sputum cells with a spectrum of differential DNA methylation phenotypes (5mC/DAPI texture features) that correlate with cell morphology (epithelial and mesenchymal cell phenotypes) and growth behavior (high-proliferative cancer cells, moderately growing normal cells, and growth-arrested senescent cells).

Although lung cancer cells are one type of cancer cells that could be detected according to the methods described herein, analysis of 5mC content and/or 5mC and gDNA spatial nuclear co-distribution could be used to detect any cancer cell.

With the foregoing additional background in mind, certain specific non-limiting embodiments are described below.

In various embodiments, the invention teaches a method for determining if a cell is cancerous or precancerous. In some embodiments, the method comprises, consists of, or consists essentially of determining the 5-methylcytosine (5mC) content and/or spatial nuclear co-distribution of 5mC and global DNA (gDNA) in a nucleus of the cell; and determining that the cell is cancerous or precancerous if the 5mC content and/or spatial nuclear co-distribution of 5mC and gDNA in the nucleus of the cell is significantly different from a non-cancerous or non-precancerous reference cell and/or a non-cancerous or non-precancerous reference cell population, or determining that the cell is not cancerous or not precancerous if the 5mC content and/or spatial nuclear co-distribution of 5mC and gDNA are not significantly different from those of a non-cancerous or non-precancerous reference cell and/or a non-cancerous or non-precancerous reference cell population. In this context, a significant difference is defined as equal to or higher than 25% in 5mC content, and/or equal to or higher than 20 degrees in the angle of the regression line (also called trendline) herein referred to as or 6 or 0, whereby cancerous or pre-cancerous cells exhibit less 5mC content and/or a smaller regression-line angle of the 5mC/DAPI colocalization scatter plot, compared to a reference non-cancerous or non-precancerous cell or non-cancerous or non-precancerous population of cells: when the DAPI-values define the x-axis and the 5mC values define the y-axis. In some embodiments, 25-99%, or 30-80%, or 40-60% difference in 5mC content is significant. In some embodiments, 20-90 degrees, or 30-80 degrees, or 40-70 degrees, or 50-60 degrees in the angle of the regression line is significant. In certain embodiments, the cell is determined to be cancerous or precancerous if the 5mC content is significantly lower than the non-cancerous or non-precancerous reference cell and/or non-cancerous or non-precancerous reference cell population. In certain embodiments, the cell is obtained from a biological sample. In some embodiments, the biological sample includes sputum. In certain embodiments, the sputum includes respiratory cells. In some embodiments, the origin of the cancerous cell or precancerous cell is of the upper aerodigestive tract, which includes a cell associated with any anatomical structure or set of structures in the path from the lungs to the lips or nares of the nose. This may include, but is in no way limited to cells of the lungs, trachea, esophagus, mouth, nose, and sinuses. In some embodiments, the cancerous cell or precancerous cell is of lung cancer origin. In some embodiments, the cancerous cell or precancerous cell is of a lung tumor origin. In some embodiments the cancerous cell or precancerous cell is of an esophageal origin. In certain embodiments, the biological sample is obtained from a subject who has a history of smoking cigarettes. In some embodiments, the biological sample is obtained from a subject who does not have a history of smoking cigarettes. In various embodiments, the biological sample is obtained from a subject who has received a lung cancer treatment that may include, but is in no way limited to radiation therapy, chemotherapy, surgery, and combinations thereof. In some embodiments, the biological sample is obtained from a subject who has not received lung cancer treatment. In certain embodiments, the global 5mC and gDNA contents of individual cell nuclei, as well as the spatial nuclear co-distribution of 5mC and gDNA are determined with a microscope after the cell has been subjected to (a) immunofluorescence staining with an antibody specific for 5mC, and (b) counterstaining with 4',6-diamidino-2-phenylindole (DAPI).

Any commercially available monoclonal antibody specific for 5mC could be utilized in conjunction with the inventive methods described herein. For example, the 5mC antibody could be obtained from vendors such as Aviva Systems Biology, Corp. (San Diego, Calif.), GeneTex, Inc. (Irvine, Calif.), Active Motif, Inc. (Carslbad, Calif.), and Diagenode, Inc. (Denville, N.J.) to name a few. In some embodiments, the 5mC antibody is the antibody described in Reynaud C, Bruno C, Boullanger P, Grange J, Barbesti S, Niveleau A. Monitoring of urinary excretion of modified nucleosides in cancer patients using a set of six monoclonal antibodies. Cancer Lett 1992 Mar. 31; 63(1):81, which is hereby incorporated herein by reference in its entirety as though fully set forth.

In certain embodiments the phenotypes of individual sputum-derived cells is determined with a microscope after the cells have been subjected to immunofluorescence staining with antibodies against cell-type specific markers. These include but are not restricted to antibodies specific for cytokeratins and cell surface molecules.

In some embodiments, the sputum sample described above was obtained from a subject by a method including administering hypertonic saline into the subject's respiratory tract; and collecting a quantity of sputum that is expelled from the subject as the result of inhaling said hypertonic saline. In certain embodiments, the hypertonic saline is administered via an ultrasonic nebulizer or a non-ultrasonic nebulizer. In some embodiments, the hypertonic saline is 3-5% NaCl.

In embodiments of the invention in which visualization and/or quantification of 5mC content, gDNA, and/or spatial nuclear co-distribution of 5mC and gDNA is required, these features may be visualized and/or quantified through the use of optical imaging systems such as widefield epifluorescence microscopes and scanners, confocal microscopes and scanners, multi-photon microscopes and scanners, and super-resolution microscopes (nanoscopes) and scanners, as well as combinatorial modalities thereof. In some embodiments, a microscope is used for this visualization and/or quantification. In certain embodiments, the microscope is a confocal scanning microscope. In some embodiments, the confocal scanning microscope has a lateral resolution (in x- and y-axes) in the range of 100-200 nm and a vertical resolution (in z-axis) of approximately 500 nm In various embodiments, the invention teaches a method that comprises, consists of, or consists essentially of obtaining a biological sample from a subject, wherein the biological sample includes a cell; determining a 5-methylcytosine (5mC) content and/or spatial nuclear co-distribution of 5mC and global DNA (gDNA) in a nucleus of the cell; determining that the cell is cancerous or precancerous if the 5mC content and/or spatial nuclear co-distribution of 5mC and gDNA in the nucleus of the cell is significantly different from a non-cancerous or non-precancerous reference cell and/or non-cancerous or non-precancerous cell population; and treating the subject for cancer according to any method described herein if it is determined that the cell is cancerous or precancerous. In some embodiments, if a subject is determined to have a cancerous or precancerous condition, then the subject is monitored for disease progression, rather than implementing treatment. In some embodiments, the cancerous cell or precancerous cell originates in the aerodigestive tract, as described herein. In certain embodiments, the biological sample includes sputum. In some embodiments, the sputum includes respiratory cells. In certain embodiments, the cancerous cell or precancerous cell is of lung cancer origin. In some embodiments, the subject has been previously treated for cancer, including any cancer type described herein. In some embodiments, the subject has not been previously treated for cancer, including any cancer type described herein. In some embodiments, the subject has a history of smoking cigarettes. In certain embodiments, the subject does not have a history of smoking cigarettes.

In various embodiments, the invention teaches a method for determining the presence or absence of a cancerous cell or a precancerous cell in a biological sample that includes a plurality of cells. In some embodiments, the method includes: utilizing high-resolution imaging to determine 5-methylcytosine (5mC) load/content and/or spatial nuclear co-distribution of 5mC and global DNA (gDNA) for each of a plurality of cells in the biological sample; and optionally determining cell population heterogeneity for the plurality of cells based on said MeC load and spatial nuclear co-distribution of 5mC and gDNA. In certain embodiments, it is determined that a cancerous cell or precancerous cell is present in the biological sample if 5mC load and/or spatial nuclear co-distribution of 5mC and gDNA in any cell in the biological sample is significantly different from a non-cancerous or non-precancerous reference cell population and/or any cell in the biological sample is significantly different with respect to 5mC load and/or spatial nuclear co-distribution of 5mC and gDNA compared to the global pattern of the entire population of cells visualized in the biological sample. In some embodiments, it is determined that a cancerous cell or precancerous cell is not present in the biological sample if the 5mC load and/or spatial nuclear co-distribution of 5mC and gDNA are not significantly different from those of a non-cancerous or non-precancerous reference cell population and/or no cell in the biological sample is significantly different with respect to 5mC load and/or spatial nuclear co-distribution of 5mC and gDNA compared to the global pattern of the entire cell population in the biological sample. In some embodiments, the biological sample includes sputum. In certain embodiments, the sputum includes respiratory cells. In some embodiments, the cancerous cell or precancerous cell detected/determined is associated with lung cancer. In certain embodiments, the cancerous cell or precancerous cell detected/determined is associated with non-small cell lung cancer (NSCLC). In certain embodiments, the method can be used to diagnose a subject with lung cancer, including NSCLC, at any stage, on the basis of the presence of a cancerous cell in the biological sample. In certain embodiments, the sputum is obtained from a subject who has a history of smoking cigarettes. In some embodiments, the sputum is obtained from a subject who has received any lung cancer treatment including but in no way limited to radiation therapy, chemotherapy, surgery, and combinations thereof. In some embodiments, the sputum is obtained from a subject who has not received one or more of the above-described cancer treatments. In some embodiments, the sputum is obtained from a subject who has not received treatment for cancer. In some embodiments, the sputum is obtained from an individual who has never been diagnosed with cancer. In certain embodiments, 5mC patterns are visualized after immunofluorescence staining with an antibody specific for 5mC. In some embodiments, gDNA is visualized after counterstaining with 4',6-diamidino-2-phenylindole (DAPI).

In certain embodiments, the invention teaches quantifying the number of cells in the sample that have been identified as cancerous or precancerous by implementing the foregoing testing methods, and comparing that number of cancerous or precancerous cells to a reference number of cancerous or precancerous cells in individuals who have cancer, or precancer, and/or comparing the tested sample with a reference number of cancerous or precancerous cells in individuals who do not have cancer, or pre-cancer.

In certain embodiments, the inventive methods described herein include obtaining the sputum sample from the subject. In some embodiments, the sputum sample is obtained by administering hypertonic saline into the subject's respiratory tract; and collecting a quantity of sputum that is expelled from the subject as the result of inhaling said hypertonic saline. In certain embodiments, the hypertonic saline is administered via an ultrasonic nebulizer. In some embodiments, the hypertonic saline is about 3 to 5% NaCl. In some embodiments, the ultrasonic nebulizer has an output of about 1 to 2 mL/minute. In some embodiments the saline solution is inhaled for a period of about 5 to 20 minutes. In some alternative embodiments, the sputum sample is obtained by using a handheld nebulizer to dispense hypertonic saline into the subject's respiratory tract. In some embodiments, the hypertonic saline is within a range of NaCl described above. In some embodiments, the hypertonic saline is dispensed for a period of time within a range described above.

While the administration of hypertonic saline is one method of inducing sputum, one would readily appreciate that alternative methods of inducing sputum could also be used to obtain a sample that could be used with the inventive methods. Merely by way of non-limiting examples, bronchoscopy and bronchoalveolar lavage could also be used.

In various embodiments, the invention teaches a method for treating a subject who has been diagnosed with cancer or a precancerous condition according to one or more of the methods described herein. In some embodiments, the method comprises, consists of, or consists essentially of administering chemotherapy and/or radiation therapy and/or performing surgery to resect all or a portion of a tumor on the subject, wherein the subject was diagnosed with cancer or a precancerous condition via any method described herein. In some embodiments, the subject has been diagnosed with lung cancer.

Although the foregoing methods are aimed at detecting lung cancer and pre-cancerous lesions in a subject, as indicated above it would also be possible to utilize the same basic principles of the inventive methods described herein to analyze samples and detect cancer or pre-cancerous lesions of different origins. Merely by way of non-limiting examples, saliva and/or mucous secretions could be assayed to determine the presence or absence of head and/or neck cancer; colon and/or rectal secretions could be assayed to determine the presence or absence of colon and/or rectal cancer; cervical secretions could be assayed to determine the presence or absence of cervical cancer; vaginal and/or cervical secretions could be assayed to determine the presence or absence of ovarian cancer, and fluids from the urethra could be assayed to determine the presence or absence of urethral, bladder or kidney cancer.

Further, although tests involving 5mC are the primary focus of the examples described herein, one of skill in the art would readily appreciate that other cytosine variations, such as 3-methylcytosine, 5-hydroxymethylcytosine, 5-formylcytosine, and 5-carboxylcytosine could also be used as bases for distinguishing between cancerous (or precancerous) and noncancerous cells, by applying essentially the same detection and analysis methods described herein. Therefore, evaluation of any cytosine methylation, by using the methods described herein, is intended to be within the scope of the present application. Moreover, although tests described in the specific examples set forth herein involve DAPI as the primary dye for delineating gDNA as well as the nuclear volume, one of skill in the art would also appreciate that other dyes, which bind double-stranded DNA in a nonsequence-specific manner and can be used for gDNA quantification. These may include but are not limited to propidium iodide, the Hoechst dyes (including Hoechst 33258 and Hoechst 33342), ethidium bromide, SYBR Green, SYBR Gold, Pico Green, the SYTOX dyes (including SYTOX Green, SYTOX Blue, and SYTOX Orange), the SYTO dyes, the YOYO and TOTO families of dyes (including YOYO, TOTO, JOJO, BOBO, POPO, YO-PRO, and PO-PRO), as well as actinomycin D and 7-aminoactinomycin D (7-AAD), which could also be used for the same purposes.

Given the significant difference in global nuclear 5mC load and distribution between pre-cancerous or cancerous cells and their normal counterparts, these differences can be visualized and measured using light microscopy in a rapid, parallel manner at single-cell resolution for the characterization of thousands of cells within biological samples. In some embodiments, the global nuclear content and relative distribution of 5mC versus global gDNA (delineated by DAPI) in sputum-derived cells and cell populations are analyzed. These nuclear entities are not static and reorganize during cellular transformation of normal healthy cells into precancerous and cancerous cells. In this context, a powerful aspect of scatter plots is their ability to depict mixture models of simple relationships between variables. These relationships can reflect cellular patterns as specific signatures, in which the variables can be nuclear structures as shown in the case of nuclear 5mC patterns versus DAPI-stained gDNA (Tajbakhsh J, Wawrowsky K A, Gertych A, Bar-Nur O, Vishnevsky E, Lindsley E H, Farkas D L). Characterization of tumor cells and stem cells by differential nuclear methyl-ation imaging. In: Farkas D L, Nicolau D V, Leif R C, editors. Proceedings Vol. 6859 Imaging, Manipulation, and Analysis of Biomolecules, Cells, and Tissues VI 2008. p 68590F). We have shown that such reorganizations can be dynamically monitored by scatter plotting the signal distributions of global 5mC and gDNA, with their differential distribution becoming visible as changes in the plotted patterns. In other words, the 2D scatter plots represent signal frequency co-distributions of the targeted two nuclear entities, and the co-distribution plots can be considered as cell-specific signatures (See Tajbakhsh J, Wawrowsky K A, Gertych A, Bar-Nur O, Vishnevsky E, Lindsley E H, Farkas D L). Characterization of tumor cells and stem cells by differential nuclear methyl-ation imaging. In: Farkas D L, Nicolau D V, Leif R C, editors. Proceedings Vol. 6859 Imaging, Manipulation, and Analysis of Biomolecules, Cells, and Tissues VI 2008. p 68590F); Gertych A, et al. Automated quantification of DNA demethylation effects in cells via 3D mapping of nuclear signatures and population homogeneity assessment. Cytometry A 2009; 75:569-83; Gertych A, et al. Measuring topology of low-intensity DNA methylation sites for high-throughput assessment of epigenetic drug-induced effects in cancer cells. Exp Cell Res 2010; 316(19):3150-60; Oh J H, et al. Nuclear DNA methylation and chromatin condensation phenotypes are distinct between normally proliferating/aging, rapidly growing/immortal, and senescent cells. Oncotarget 2013; 4:474-93. In some embodiments, these 5mC/gDNA codistribution signatures together with the content of global 5mC and gDNA are the three parameters/biomarkers that are considered in the characterization of sputum-derived individual cells and cell populations for the identification of pre-cancerous and cancerous cells.

One skilled in the art will recognize many methods and materials similar or equivalent to those described herein, which could be used in the practice of the present invention. Indeed, the present invention is in no way limited to the methods and materials described.

EXAMPLES

Example 1

Additional Background

Lung Cancer and Current State of Diagnosis

In the year 2010, there were over 200,000 new cases of lung cancer reported in the United States, accounting for 15% of all new cancer cases. The estimated number of lung cancer deaths in the same period was roughly 160,000, representing ~28% of all cancer-related deaths. Unfortunately, due to limited treatment options, lung cancer is the most common cause of cancer related mortality. If this disease is diagnosed in an early stage, a complete surgical resection of the tumor provides a favorable chance for cure. Therefore, early detection of this disease has been the focus of many attempts in the past few decades. Several trials utilizing radiographical techniques including chest X-ray, chest computed tomography (CT), and positron emission tomography (PET) scans have shown mixed results with unclear clinical benefits and harbor very high cost. As indicated above, radiographical methods for early detection of lung cancer, including chest CT scans, involve a high dose of radiation, which by itself imposes a higher risk of developing secondary malignancies if used frequently. As a result, frequent use of chest CT scans for screening lung cancer is probably not safe or economical.

Importantly, previous trials have utilized sputum cytology for early detection of lung cancer, but they mainly depended on evaluating morphological changes of exfoliated epithelial respiratory cells, and each of them failed to detect lung cancer cases to the point that could show a meaningful clinical advantage.

On the other hand, assessment of methylation status of certain genes in the sputum samples of high-risk patients has been successful in early detection of lung cancer lesions. Unfortunately, lung cancer is a heterogeneous group of diseases and no uniform abnormality is identified in all cases. Equally important, the analysis of cell samples that average gene methylation status across a large number of cells may disguise the important subtle information that is specific to a smaller subgroup of cancerous cells in sputum and therefore bias the analysis results. Therefore, relying on the abnormalities of a subset of genes across all sputum cells to detect lung tumors probably may only cover a subgroup of cases. After considering the shortcomings of previously available diagnostic methods, the inventors sought to analyze the global DNA methylation status of exfoliated respiratory cells in the sputum in a cell-by-cell fashion as a tool for early detection of lung cancer.

DNA Methylation in Cancer Diagnosis

The perfect epigenetic equilibrium of normal cells is substantially altered when cells become transformed. The resulting epigenetic alterations at the DNA level fall into two categories: (i) gene-specific hypermethylation of CpGs in gene promoters in gene-rich genomic regions termed CpG-islands, and (ii) genome-wide hypomethylation, a large percentage of which occurs in repetitive DNA elements. Aberrant methylation patterns are associated with several cancer types. Genome-wide hypomethylation parallels closely to the degree of malignancy and is a ubiquitous finding. The analysis of DNA hypomethylation has largely remained unexploited. Cancer cell lines, widely used as research models, exhibit a large variation in genome-wide demethylation, which reflects tissue-specificity and unlikely results from stochastic processes. A malignant cell can contain 20-60% less genomic methylcytosine than its normal counterpart. The loss of methyl groups is achieved mainly by hypomethylation of repetitive DNA sequences, which account for more than 90% of the human genome, including transposable elements (~48% of genome) such as short and long interspersed nuclear elements (SINES and LINES, respectively), largely acquired as retroviruses throughout evolution. Global methylation is also clinically relevant, as demonstrated by associations between clinical outcome and global methylation levels in a number of cancer types. Global hypomethylation seems to be related to cancer progression, since loss of global methylation tends to become more pronounced as precancerous lesions progress. To date, differential DNA methylation analysis has been quantitatively assessed mostly by molecular approaches including electrophoretic, chromatographic, PCR-based, array-based, and sequencing technologies. Despite tremendous improvement in specificity, sensitivity, and the inherent single-base resolution of these methods, they remain technically challenging in the high-throughput analysis of single cells. These include the limitation of PCR-based approaches in multiplexing, and the challenging sensitivity and cost issues of whole-genome sequencing, especially for the interrogation of repetitive elements. Alternatively, and considering the prevalence and load of DNA methylation imbalances, especially hypomethylation of repetitive elements, imaging-based assessment of global nuclear 5mC patterns provides a powerful tool to simultaneously analyze and characterize a large number of cells, as the underlying molecular processes involve large-scale chromatin reorganization visible by light microscopy.

Significance of Quantitative DNA Methylation Imaging

Figure 1:
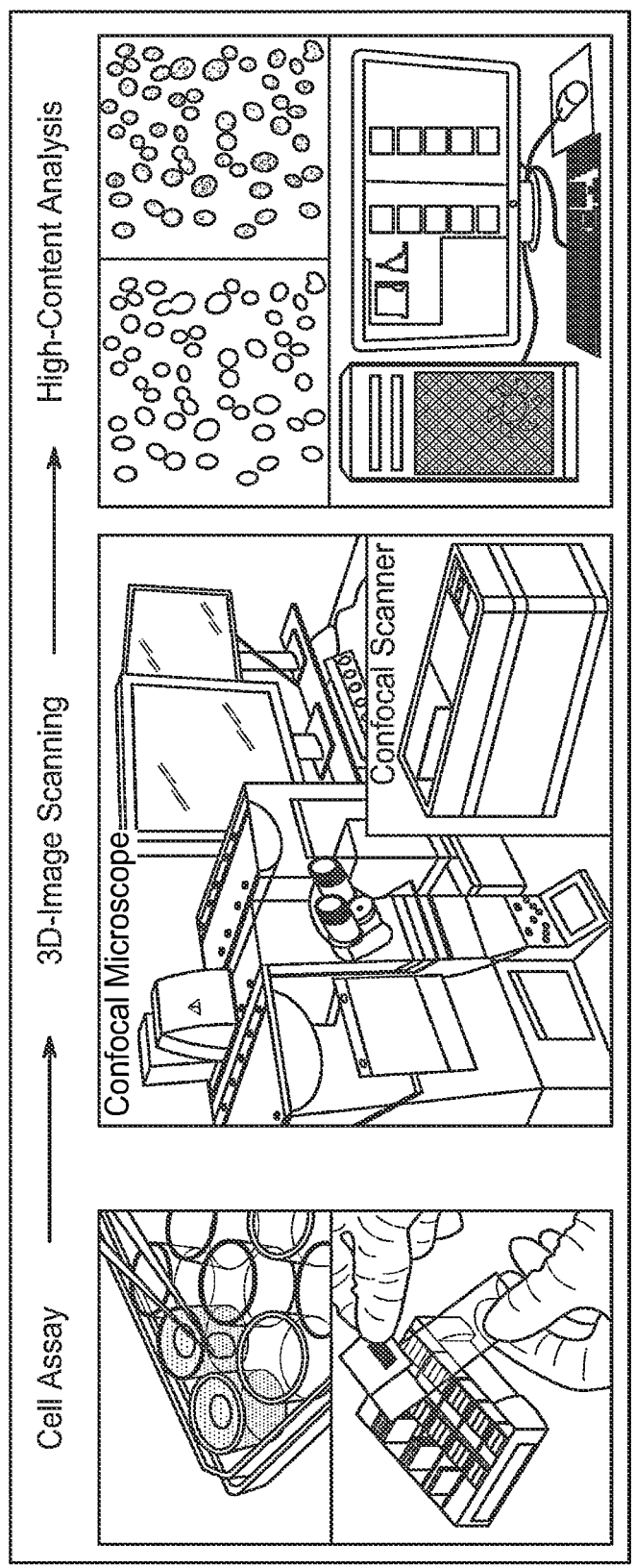
FIG. 1 demonstrates, in accordance with an embodiment of the invention, the workflow of 3D quantitative DNA Methylation Imaging (3D-qDMI) includes three steps: (1)

As demonstrated herein, a method of quantitative DNA methylation imaging (3D-qDMI) has been developed and applied to lung cancer. This nondestructive method entails the parallel quantitative measurement of 5-methylcytosine load and spatial nuclear distribution, in order to characterize cells and tissues (See Tajbakhsh J, et al. Characterization of tumor cells and stem cells by differential nuclear methylation imaging. In: Farkas D L, Nicolau D V, Leif R C, eds. Imaging, Manipulation, and Analysis of Biomolecules, Cells, and Tissues. San Jose, Calif.: Proceedings of the SPIE 2008; 6856:6859F1-10; Gertych A, et al. Automated quantification of DNA demethylation effects in cells via 3D mapping of nuclear signatures and population homogeneity assessment. Cytometry A 2009; 75:569-83; Gertych A, et al. Measuring topology of low-intensity DNA methylation sites for high-throughput assessment of epigenetic drug-induced effects in cancer cells. Exp Cell Res 2010; 316:3150-60; Gertych A, et al. Homogeneity assessment of cell populations for high-content screening platforms. In: Information Technology in Biomedicine. Vol. 2. Advances in intelligent and soft computing, Vol. 69. Ewa Pietka and Jacek Kawa, Editors, Springer Verlag, Heidelberg, Germany; Tajbakhsh, J. et al. (2012). 3-D Quantitative DNA Methylation Imaging for Chromatin Texture Analysis in Pharmacoepigenomics and Toxicoepigenomics. In Epigenomics: From Chromatin Biology to Therapeutics. K. Appasani, editor. Cambridge University Press, Cambridge, United Kingdom; each of which is incorporated herein by reference in its entirety as though fully set forth). The workflow of an embodiment of 3D-qDMI is illustrated in FIG. 1.

Given the large dynamic range in 5mC load and distribution, 3D-qDMI allows for the rapid, parallel, morphometric, single-cell resolution characterization of thousands of cells within heterogeneous sputum samples. The following highlights some of the advantages of 3D-qDMI applicable to using non-invasive surrogates such as sputum samples in lung cancer diagnostics and clinical decision-making: (i) 3D-qDMI does not require cellular enrichment through error-prone separation methods; (ii) the method does not require time-consuming DNA extraction and DNA amplification, (iii) 3D-qDMI provides cell-by-cell analysis; (iv) the method enables the heterogeneity assessment of cell populations, including frequency of different cell types in regards to DNA methylation features; (v) irrelevant cells can be identified and excluded from analysis, which would prevent data skewing through sample impurity by infiltrating hematopoietic cells; (vi) the cost-efficient cytometric approach can be automated and is amenable to scale, therefore can be easily developed and implemented in clinical settings. The cytometric approach can be applied to simultaneous multicolor high-content imaging. Hence, cells of interest and/or infiltrating hematopoietic cells can be additionally labeled for cell-specific markers. Subsequently, irrelevant cells can be identified in the output data and eliminated before data analysis. Furthermore, the method is compatible with using microscopic slides and Society for Biomolecular Sciences (SBS)-format microplates as a support for deposition of sputum-derived cells. Therefore, the method has the potential for implementation in the high-throughput clinical and diagnostic environment, that is routinely applying said formats for cancer diagnostics. In detail, the three steps of sample preparation, staining, and scanning can be automated with existing commercially available high-throughput instruments. Image and data analysis are computerized processes that are naturally performed in an automated fashion, and only limited by computational capacity.

Analysis of Samples

The 3D-qDMI software implemented in certain embodiments described herein was designed to perform sophisticated 3-D image analysis of individual cells (as opposed to the collective analysis and result-output) within an image frame, thus allowing flexible elimination and combination of cells for variable statistics. In some embodiments, the outcome of the 5mC/DAPI colocalization pattern can be represented as a scatter plot (See FIG. 2). However, one of skill in the art would readily appreciate that there are many other ways to represent this type of data.

As demonstrated in FIG. 2, 5mC features such as 5mC/DAPI colocalization patterns can vary between cells within a population. Therefore, cell population heterogeneity assessment is a valuable feature in determining the composition of the cells, i.e. the degree of phenotypic variation important for the identification of a low number of cells that may show aberrant MeC phenotypes similar to aggressive cancer cells. Homogeneity can be assessed by the comparison of structural similarity within an entire cell population by expressing a relationship between an individual nuclear 5mC/DAPI pattern and the global pattern of the entire cell population, representing the sum of all individual nuclear patterns (reference pattern).

Sputum Studies The inventors explored 3D nuclear 5mC patterns in human upper respiratory cells derived from the sputum of a healthy individual (non-smoker with no history of cancer), as well as sputum cells from a lung cancer patient (smoker) and matching tissue specimen, as well as three human cell lines. Cell lines included the immortalized normal human epithelial cell line (BEAS-2B), and the NSCLC lines A549 (alveolar basal epithelial cells) and H157 (highly invasive lung carcinoma cells). FIG. 4 shows normal parenchyma and the tumoral region of a fluorescently labeled section from a newly diagnosed, surgically resected lung cancer. The inventors observed common global DNA methylation patterns amongst healthy cells that significantly differ from the 5mC/DAPI patterns of cancerous cells and abnormal sputum cells from the cancer patient (FIG. 5) that were significantly globally hypomethylated. All populations of the three different cell lines and sputum-derived cells, as well as the normal tissue, showed a high degree of homogeneity (visualized through KL category maps) in terms of their 5mC/DAPI codistributions, displayed as scatter plots on the cell population level and for individual representative nuclei.

The inventors have introduced a measureable descriptor of each cell type (FIG. 5): the regression line of the plot and the upper and lower signal borderlines ML1 and ML2 are characteristic and determine the four angles $\alpha$, $\beta$, $\gamma$, and $\delta$ for each prototypic cell type. The resulting differential factor $F=[(\alpha/\gamma)\times(\beta/\delta)]$ is specific to each cell type: 0.54 (BEAS-2B), 0.42 (A549), 0.12 (H157), 0.78 (typical normal tissue cells), 0.45 (cells of normal sputum), 0.44 (majority of N1-type cells in sputum of cancer patient), 0.01 (N2-type cell in sputum of cancer patient), and 0.05 (typical cancer tissue cells). This measure underlines the differentiating power of global methylation patterns for detection of normal and malignant cells. Especially the resemblance between (N2-type) cell signatures in cancer-patient sputum and typical tumor tissue cells can play a central role in detecting abnormal cells in sputum samples, early in the process of tumorigenesis. The observations demonstrated in FIGS. 4 and 5 that 3D nuclear DNA methylation patterns serve as a novel biomarker for the non-invasive detection of malignant cells of the respiratory tract. In some aspects, the inventive method utilizes 3D-qDMI to determine differential global DNA methylation patterns of exfoliated respiratory cells in a sputum sample of individuals with higher risk for developing lung cancer. Specifically, each sputum cell population can be characterized by the statistics of determined F-factors that provide an estimation of the cell composition, which could facilitate the detection of malignant cells.

Example 2

Methods

Preparation of Cell Specimens

Sputum induction can be performed through inhalation of hypertonic saline (3 to 5% NaCl). Utilizing a nebulizer, aerosols can be generated, with an output at 1.5 mL/min. The subjects inhale saline solution aerosols for a period of up to 20 min. Subjects are encouraged to expectorate sputum after mouth rinsing with tap water every 5 minutes. Exfoliated upper respiratory cells are isolated and fixed on slides/coverslips or in microplate wells. Samples that were collected in a plastic container are kept at 4° C. until processing. Samples are diluted with phosphate-buffered saline (PBS) solution, containing 0.1% dithiothreitol (DTT) commonly known as 10% sputolysin solution, and are incubated for 20 minutes before centrifugation at 300-1500×g for 5-10 minutes at room temperature in order to separate cellular and fluid (mucus) phases. This process is repeated until the cell suspension appears to be homogeneous and clear. Then, the cell pellet is resuspended in PBS, and the cells are filtered through a 40-100 µm nylon mesh (cell strainer) to remove residual mucus and debris. Subsequently, cells are centrifuged at 300-1500×g for 5-10 minutes. The cell pellet (containing all harvested cells) is resuspended in 1-2 microliters of epithelial-cell medium, transferred onto a microscopic glass coverslip, and cultured for 16-48 hours at 37° C. and 5% $CO_2$ for the cells to attach to the coverslip. In some embodiments, cell counts are performed on samples centrifuged (cytospin) and the cell sample is spread on a microscope slide/coverslip or in a microplate well. Subsequently, cells are fixed in 4% paraformaldehyde for 15-45 minutes and are kept in PBS at 4° C. Then, characterization of fixed cells is accomplished by 3D quantitative DNA Methylation Imaging (3D-qDMI), as described herein.

As an alternative to the airway sputum processing method described above, airway sputum may be processed by any method known in the art. Merely by way of example, airway sputum processing may be performed according to any method described or referenced in Hamid et al. Eur Respir J 2002; 20 Suppl. 37, 19s-23s.

Biochemistry

Sample analysis is accomplished through the combination of immunofluorescence staining for visualization of overlay methylcytosine patterns with a specific mouse monoclonal antibody (clone 33D3) against 5-methylcytosine in cell nuclei, and counterstaining with 4',6-diamidino-2-phenylindole (DAPI) for delineation of global nuclear DNA. While there are numerous publicly available protocols for staining for visualization of 5-methylcytosine and gDNA, in some embodiments, protocols of the following references are used: Tajbakhsh J, et al. Characterization of tumor cells and stem cells by differential nuclear methylation imaging. In: Farkas D L, Nicolau D V, Leif R C, eds. Imaging, Manipulation, and Analysis of Biomolecules, Cells, and Tissues. San Jose, Calif.: Proceedings of the SPIE 2008; 6856: 6859F1-10; 33. Gertych A, et al. Automated quantification of DNA demethylation effects in cells via 3D mapping of nuclear signatures and population homogeneity assessment. Cytometry A 2009; 75:569-83; Gertych A, et al. Measuring topology of low-intensity DNA methylation sites for high-throughput assessment of epigenetic drug-induced effects in cancer cells. Exp Cell Res 2010; 316:3150-60; Gertych A, et al. Homogeneity assessment of cell populations for high-content screening platforms. In: Information Technology in Biomedicine. Vol. 2. Advances in intelligent and soft computing, Vol. 69, 2010; Gertych A, et al. 3-D DNA methylation phenotypes correlate with cytotoxicity levels in prostate and liver cancer cell models. BMC Pharmacol Toxicol. 2013 Feb. 11; 14:1; Tajbakhsh J, et al. Early In Vitro Differentiation of Mouse Definitive Endoderm is Not Correlated with Progressive Maturation of Nuclear DNA Methylation Patterns. PLoS ONE 2011; 6(7):e21861; Tajbakhsh J. Covisualization of methylcytosine, global DNA, and protein biomarkers for In Situ 3D DNA methylation phenotyping of stem cells. Methods Mol Biol. 2013; 1052:77-88; Oh J H, et al. Nuclear DNA methylation and chromatin condensation phenotypes are distinct between normally proliferating/aging, rapidly growing/immortal, and senescent cells. Oncotarget 2013; 4:474-93; Tajbakhsh J, et al. Dynamic heterogeneity of DNA methylation and hydroxymethylation in embryonic stem cell populations captured by single-cell 3D high-content analysis. Exp Cell Res. 2015; 332:190-201, each of which is incorporated herein by reference in its entirety as though fully set forth). The 5mC antibody used for staining can be as described in (wwwdotncbi.nlm.nih.gov/pubmed/?term=Reynaud%20C%5BAuthor%5D&cauthor=true&cauthor_uid=1739950) Boullanger P, Grange J, Barbesti S, Niveleau A. Monitoring of urinary excretion of modified nucleosides in cancer patients using a set of six monoclonal antibodies. Cancer Lett 1992 Mar. 31; 63(1):81. The specificity of the anti-5mC antibody can be confirmed using a DNA microarray including cytosine variants and standard control experiments in combination with immunocytochemistry. For exclusion of hematopoietic cells and especially white blood cells (leukocytes) in downstream analyses, specimens can be co-immunophenotyped with anti-CD34 and anti-CD45 antibodies. In some embodiments, the inventors also use antibodies against cytokeratins such as but not limited to CK8, CK18, and CK19 to co-label for epithelial cell markers. However, malignant respiratory cells are dispersed among a large number of normal epithelial cells (on a slide). Therefore epithelial markers may not be helpful in the distinction of normal from abnormal cells.

Immunofluorescence (IF)

The following non-limiting protocol is for convenient processing of sputum-derived cells that are captured onto 18 mm round glass cover slips (No. 1) and processed in 12-well microplates. Reagent volumes need to be adjusted for other cell supports and reaction chambers.

Day 1

(a) Fixation of Tissue Sections
1) Sputum-derived cells are fixed in 4% Paraformaldehyde (PFA)/PBS for 30-45 minutes at room temperature, then washed 3 times with PBS for 3-5 minutes at room temperature. Cells not immediately processed further shall be kept in 0.002% $NaN_3$/PBS at 2-8° C.

(b) Pre-IF Processing of the Cells
2) Wash cells for 5 minutes in PBS (2 ml).
3) Permeabilize cells with 0.5% Saponin/0.5% Triton X-100/PBS (5 ml) for 20 min at room temperature, and wash 3 times with PBS (2 ml) for 3-5 minutes at room temperature.
4) Treat cells with 100 μg/ml RNase A/PBS (0.2 ml) for 30 minutes at 37° C., and wash 3 times 3-5 minutes with PBS (2 ml) at room temperature.
5) Block tissue with 3% bovine serum albumin (BSA)/PBS (1 ml) for 30 minutes at 37° C. (prior to applying the primary antibody).

(c) First Immunofluorescence
6) Incubate tissue with primary antibody or cocktail of compatible antibodies for cell phenotyping (as example rabbit anti-CK19 polyclonal antibody, Abcam Cat. #ab15463, at 1:1000 dilution; sheep anti-CD34 polyclonal antibody, R&D Systems Cat. #AF7227, at the concentration of 1 μg/ml; and chicken anti-CD45, GeneTex Cat. #GTX82139 at 1:500 dilution) in 3% BSA/PBS (0.7 ml) overnight at 2-8° C.

Day 2
7) Wash cells 4 times for 5 minutes with 01% BSA/0.1% Tween20/PBS (2 ml) at room temperature.
8) Incubate tissue with secondary antibody (for example donkey anti-goat IgG (H+L)-Alexa 568, Invitrogen, A11057) at the concentration of 5 μg/ml each in 3% BSA/PBS (0.7 ml) for 1 hour at 37° C.
9) Wash tissue 4 times with 0.1% BSA/0.1% Tween20/PBS (2 ml) for 3-5 minutes at room temperature, and once with 0.1% BSA/PBS (2 ml).
10) Fix tissue in 4% PFA/PBS (1 ml) for 15 min at room temperature. Wash cells 3 times for 3-5 minutes with PBS.
11) Depurinate cells with 2N HCl (1 ml) for exactly 40 min at room temperature, and wash 3 times with PBS (2 ml) for 3-5 minutes at room temperature.
12) Block cells with 3% BSA/PBS (1 ml) for 30 minutes at 37 C (prior to applying the primary antibody).

(d) Second Immunofluorescence
13) Incubate cells with primary antibody (for example mouse anti-MeC, clone 33D3 mAb, Aviva Systems Biology, Cat. #AMM99021) at the concentration of 1-2 μg/ml in 3% BSA/PBS (0.7 ml) overnight at 2-8° C.

Day 3
14) Wash cells 4 times for 5 minutes with 01% BSA/0.1% Tween20/PBS (2 ml) at room temperature, and once with 0.1% BSA/PBS (2 ml).
15) Incubate cells with secondary antibody (for example donkey anti mouse Alexa488 IgG (H+L), Invitrogen A21202; and chicken anti-rabbit IgG (H+L)-Alexa 647, Invitrogen A21443) both at the concentration of 5 μg/ml in 3% BSA/PBS (0.2 ml) for 2 hours at 37° C.
16) Wash tissue 4 times with 0.1% BSA/0.1% Tween 20/PBS (5 ml) for 5 minutes and once with 0.1% BSA/PBS for 5 minutes, at room temperature.
17) Incubate tissue in 5 ml of DAPI/PB S solution (warm to room temperature) for 20 min at room temperature, then rinse for ~30 sec in PBS to rinse non-specific DAPI staining.
18) Take coverslip out of the microplate and let dry completely at room temperature or in 37° C. oven (10-30 min), in the dark.
19) Transfer 7-10 μl of mounting solution (for example Prolong-Gold, Invitrogen) onto a clean and dry glass slide section and put coverslip (with cells facing the glass slide) onto the mounting droplet (strictly avoid air bubbles).

Confirmatory Molecular Method

A confirmatory molecular method can be performed on extracted DNA from isolated cells (from selected sputum samples) in parallel to verify the image-cytometrical (3D-qDMI) 5mC feature results: (i) 5mC load and (ii) hypomethylation of repetitive DNA element classes (Alu/LINE-1/Satα/Sat2)—the major causative of global DNA hypomethylation both can be assessed by Repeat-Sequence MethyLight (See Weisenberger D J et al. Analysis of repetitive element DNA methylation by MethyLight. Nucleic Acids Res. 2005 Dec. 2; 33(21):6823-36, which is incorporated herein by reference in its entirety as though fully set forth). This method has proven to be an accurate surrogate of high-performance liquid chromatography (HPLC) or high-performance capillary electrophoresis (HPCE) in the measurement of 5mC load, which have been conventionally used for global 5mC content measurements. 5mC content measurements comparatively performed by Repeat-Seq MethyLight and 3D-qDMI has yielded very high correlations (0.86-0.96), (See Gertych A, et al. 3-D DNA methylation phenotypes correlate with cytotoxicity levels in prostate and liver cancer cell models. BMC Pharmacol Toxicol. 2013 Feb. 11; 14:11 which is incorporated herein by reference in its entirety as though fully set forth).

Image Acquisition

Image acquisition can be performed by utilizing high-resolution confocal scanning microscopy. In some non-limiting embodiments, Leica's commercial TCS SP5 X Supercontinuum microscope (Leica Microsystems) is utilized. The system provides full freedom and flexibility in excitation and emission, within the continuous range of 470 to 670 nm—in 1 nm increments. The microscope can be coupled with a 405 nm diode laser line for excitation of DAPI fluorescence. Serial optical sections can be collected at increments of 200-300 nm with a Plan-Apo 63X 1.4 oil immersion lens and pinhole size 1.0 airy unit. To avoid bleed-through, the imaging of each channel can be acquired sequentially. By way of non-limiting example, the typical image size can be ranging from 1024×1024 to 2048×2048 with a respective voxel size of around 116 nm×116 nm×230.5 nm (x, y, and z axes), and resolution of 8-16 bits per pixel in all channels. The output file format can be a series of TIFF images that can be utilized for 3D-image analysis.

3D Image Analysis 3D image analysis can be performed by the application of a dedicated algorithm developed for pattern recognition and multi-parametric high-content analysis, as described in Gertych A, et al. Automated quantification of DNA demethylation effects in cells via 3D mapping of nuclear signatures and population homogeneity assessment. Cytometry A 2009; 75:569-83; Gertych A, et al. Measuring topology of low-intensity DNA methylation sites for high-throughput assessment of epigenetic drug-induced effects in cancer cells. Exp Cell Res 2010; 316:3150-60; Gertych A, et al. (2010). Homogeneity assessment of cell populations for high-content screening platforms. In: Information Technology in Biomedicine. Vol. 2. Advances in intelligent and soft computing, Vol. 69. Ewa Pietka and Jacek Kawa, Editors, Springer Verlag, Heidelberg, Germany; and Tajbakhsh J, (2012). 3-D Quantitative DNA Methylation Imaging for Chromatin Texture Analysis in Pharmacoepigenomics and Toxicoepigenomics. In Epigenomics: From Chromatin Biology to Therapeutics. K. Appasani, editor. Cambridge University Press, Cambridge, United Kingdom, each of which is incorporated herein by reference as though fully set forth.

In some embodiments, the image analysis tool operates in three steps: 1) all cells (within imaged populations) are processed for 3D segmentation; 2) fluorescence signal residing within the nuclei are measured for (a) determining the 5-methylcytosine load of the entire nucleus, (b) for the generation of codistribution maps (scatter plots) of 5mC signals and global nuclear DNA (visualized by DAPI), and c) for the variability/heterogeneity regarding the two first 5mC features. Similarity analysis is conducted of DNA methylation load and created 2D diagrams among all cells within each specimen, and cell population homogeneity is determined.

With respect to similarity analysis, commonly applied similarity measures can be organized into three groups according to object representation: (a) point-based, including Euclidean and Minkowski distances, (b) set-based including Jaccard's, Tanimoto's, and Dice's indices, and (c) probabilistic with Bhattacharyya, Kullback-Leibler's, and correlation-based Mahalanobis distances, respectively (See Dice L R. Measures of the amount of ecological association between species. J Ecology 1945; 26:297-302; Bhattacharyya A. On a measure of divergence between two statistical populations defined by probability distributions. Bull Calcutta Math Soc 1943; 35:99-109; Mahalanobis P C. On the generalized distance in statistics. Proc Nat Inst Scien India 1936; 2:49-55; Kullback S, Leibler R A. (1951), "On Information and Sufficiency". *Annals of Mathematical Statistics* 22 (1): 79-86; Jaccard P. (1912), "The distribution of the flora in the alpine zone", *New Phytologist* 11: 37-50; Rogers D J, Tanimoto T T. (1960), "A Computer Program for Classifying Plants". *Science* 132 (3434): 1115-1118; Elena Deza & Michel Marie Deza (2009) *Encyclopedia of Distances*, page 94, Springer; Levandowsky M, Winter D. (1971), "Distance between sets", *Nature* 234 (5): 34-35, all of which are incorporated herein by reference in their entirety as though fully set forth).

As indicated above, in one non-limiting example, Kullback-Leibler's (KL) divergence measurement, a mathematical operation found very suitable for the analysis of nuclear targets that have no rigid geometrical shape and position, can be used (See Gertych A, et al. Automated quantification of DNA demethylation effects in cells via 3D mapping of nuclear signatures and population homogeneity assessment. Cytometry A 2009; 75:569-83, which is incorporated herein by reference in its entirety as though fully set forth). KL divergence can be applied as a similarity measure between the normalized scatter plots of individual nuclei and a reference scatter plot to allow intra-population assessment of cells. To make the KL-values more descriptive, four soft-qualifiers can be introduced in the software, defining the similarity degree of a cell versus the entire cell population. These degrees can be associated with particular ranges of KL divergences such as: similar $KL \in [0,0.5)$, likely similar $KL \in [0.5,2)$, unlikely similar $KL \in [2,4.5)$, and dissimilar for $KL \in [4.5,\infty)$ (FIG. 3).

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A method, comprising:
    obtaining a biological sample from a subject, the biological sample including a plurality of cells;
    determining a 5-methylcytosine (5mC) content and a global DNA (gDNA) content in a nucleus of each of the plurality of cells;
    generating and displaying a scatter plotting of the 5mC content and gDNA-content for the nucleus;
    determining a spatial nuclear co-distribution of the 5mC content and gDNA content in the nucleus of each of the plurality of cells;
    determining that a cell of the plurality of cells is hypomethylated if:
    the 5mC content in the nucleus of the cell is lower than a 5mC content from one or more non-cancerous or non-precancerous reference cells by 25% or more; and/or
    a regression-line angle of the scatter plotting is smaller than a regression-line angle of a scatter plotting in the one or more non-cancerous or non-precancerous reference cells, when the gDNA content defines x-axis, the 5mC content defines y-axis, and the regression-line angle is with the x-axis of the scatter plotting;
    based at least in part on a percentage of determined hypomethylated cells in the plurality of cells exceeding a threshold, determining that the subject has a high risk of developing clinically verifiable cancer; and
    treating the subject for cancer by (i) administering chemotherapy, (ii) administering radiation therapy, (iii) performing surgery, or (iv) any combination thereof.

2. The method of claim 1, wherein the biological sample comprises sputum.

3. The method of claim 2, wherein the sputum comprises the plurality of cells.

4. The method of claim 3, wherein the plurality of cells is of lung origin.

5. The method of claim 2, wherein the subject has a history of smoking cigarettes.

6. The method of claim 2, wherein the subject does not have a history of smoking cigarettes.

7. The method of claim 1, wherein the 5mC content is determined with a microscope after the plurality of cells has been subjected to (a) immunofluorescence staining with an antibody specific for 5mC and a dye to delineate the cytoplasm, and (b) counterstaining with 4',6-diamidino-2-phenylindole (DAPI).

8. The method of claim 1, wherein the spatial nuclear co-distribution of 5mC and gDNA is determined with a microscope after the plurality of cells has been subjected to (a) immunofluorescence staining with an antibody specific for 5mC and a dye to delineate the cytoplasm, and (b) counterstaining with 4',6-diamidino-2-phenylindole (DAPI).

9. The method of claim 2, wherein the biological sample is obtained from a subject by a method comprising:
    administering hypertonic saline into the subject's respiratory tract; and
    collecting a quantity of sputum that is expelled from the subject as the result of inhaling said hypertonic saline.

10. The method of claim 9, wherein the hypertonic saline is administered via a nebulizer.

11. The method of claim 10, wherein the hypertonic saline is 3-5% NaCl.

12. The method of claim 7, wherein the microscope is a confocal scanning microscope with a resolution equal to or less than 500 nanometers.

13. The method of claim 1, wherein the plurality of cells for determining the hypomethylated cells is a plurality of human respiratory cells.

14. The method of claim 1, further comprising:
    subjecting the cell to immunofluorescence staining prior to determining the 5mC content; and then,
    subjecting the cell to counterstaining prior to determining the spatial nuclear co-distribution of the 5mC content and gDNA.

15. The method of claim 1, wherein the regression-line angle of the scatter plotting for the cell determined to be hypomethylated is less than 45°.

16. The method of claim 15, wherein the regression-line angle of the scatter plotting in the one or more non-cancerous or non-precancerous reference cells is more than 45°.

17. The method of claim 15, wherein the regression-line angle of the scatter plotting for the cell determined to be hypomethylated is less than 20°.

18. The method of claim 1, further comprising:
generating a first image of the 5mC content in the nucleus of each of the plurality of cells by utilizing high-resolution confocal scanning microscopy;
generating a second image of the gDNA content in the nucleus of each of the plurality of cells by utilizing high-resolution confocal scanning microscopy;
loading image stacks from the first and second images to a computer system configured with image analysis software to extract nuclear 5mC/gDNA patterns; and
displaying the scatter plotting of the 5mC content and global DNA (gDNA) content for the nucleus on a display based on the extracted nuclear 5mC/gDNA patterns.

* * * * *